United States Patent
LeBlanc et al.

(10) Patent No.: US 7,417,223 B2
(45) Date of Patent: Aug. 26, 2008

(54) METHOD, SYSTEM AND COMPUTER SOFTWARE PRODUCT FOR SPECIFIC IDENTIFICATION OF REACTION PAIRS ASSOCIATED BY SPECIFIC NEUTRAL DIFFERENCES

(75) Inventors: Yves LeBlanc, Ontario (CA); Nic Bloomfield, Newmarket (CA)

(73) Assignees: MDS Inc., Concord (CA); Applera Corporation CT (US)

(*) Notice: Subject to any disclaimer, the term of this patent is extended or adjusted under 35 U.S.C. 154(b) by 234 days.

(21) Appl. No.: 11/260,222

(22) Filed: Oct. 28, 2005

(65) Prior Publication Data
US 2007/0096021 A1 May 3, 2007

(51) Int. Cl.
G01N 27/00 (2006.01)
G01N 30/72 (2006.01)
G01N 37/00 (2006.01)
H01J 49/02 (2006.01)
H01J 49/26 (2006.01)

(52) U.S. Cl. .............. 250/282; 250/281; 250/286; 250/287; 250/299

(58) Field of Classification Search .............. 250/282
See application file for complete search history.

(56) References Cited

U.S. PATENT DOCUMENTS

| | | | | |
|---|---|---|---|---|
| 5,058,602 | A * | 10/1991 | Brody | 600/546 |
| 5,073,713 | A * | 12/1991 | Smith et al. | 250/282 |
| 5,274,233 | A * | 12/1993 | Kelley | 250/282 |
| 6,586,727 | B2 | 7/2003 | Bateman et al. | |
| 6,770,871 | B1 * | 8/2004 | Wang et al. | 250/281 |
| 6,781,117 | B1 | 8/2004 | Willoughby et al. | |
| 6,908,740 | B2 * | 6/2005 | Vandekerckhove et al. | 435/7.1 |
| 7,009,174 | B2 * | 3/2006 | Le Blanc | 250/281 |
| 7,049,581 | B2 * | 5/2006 | Whitney et al. | 250/282 |
| 7,157,700 | B2 * | 1/2007 | Kaufman et al. | 250/286 |
| 7,198,896 | B2 * | 4/2007 | Rush et al. | 435/6 |
| 7,230,233 | B2 * | 6/2007 | Whitney et al. | 250/282 |
| 2002/0063206 | A1 | 5/2002 | Batemen et al. | |
| 2004/0251409 | A1 | 12/2004 | Le Blanc | |
| 2006/0169892 | A1 * | 8/2006 | Baba et al | 250/292 |

(Continued)

FOREIGN PATENT DOCUMENTS

EP 1 220 290 A2 7/2002

(Continued)

OTHER PUBLICATIONS

International Search Report from the Canadian Intellectual Proper Office Oct. 19, 2006.

(Continued)

Primary Examiner—David A. Vanore
Assistant Examiner—Bernard E Souw
(74) Attorney, Agent, or Firm—Bereskin & Parr (57) ABSTRACT

A first mass spectrum and a second mass spectrum of the same ion sample can be analyzed to determine reaction pairs. These reaction pairs are determined based on a selected neutral difference by shifting the second mass spectrum by the neutral difference relative to the first mass spectrum to provide a shifted mass spectrum. Then, the shifted mass spectrum is compared with the first mass spectrum of the ion sample to determine the reaction pairs based on the neutral difference.

25 Claims, 10 Drawing Sheets

U.S. PATENT DOCUMENTS

2006/0284069 A1* 12/2006 Le Blanc .................... 250/282
2007/0096021 A1* 5/2007 LeBlanc et al. ............. 250/282

FOREIGN PATENT DOCUMENTS

| EP | 1 225 618 A2 | 7/2002 |
| EP | 1385194 | 1/2004 |
| JP | 03165446 | 7/1991 |

OTHER PUBLICATIONS

Written Opinion of the International Searching Authority from the Canadian Intellectual Property Ofice Oct. 19, 2006.

Hoffman M.D., Sniatynski, M.J., Rogalski, J.C., Le Blanc, Y., Kast, J.; Multiple Neutral Loss Monitoring (MNM): A Multiplexed Method for Post-translation Modification Screening; *Journal of the American Society for Mass Spectrometry*, vol. 17, Issue 3, Mar. 2006, pp. 307-317.

Owen, K.G. Department of Chemistry, Drexel University, Philadelphia, Pennsylvania 19104; Application of Correlation Analysis Techniques to Mass Spectral Data; *Applied Spectroscopy Reviews*, 27(1), 1-49 (1992), Copyright© 1992 by Marcel Dekker, Inc.

* cited by examiner

METHOD, SYSTEM AND COMPUTER SOFTWARE PRODUCT FOR SPECIFIC IDENTIFICATION OF REACTION PAIRS ASSOCIATED BY SPECIFIC NEUTRAL DIFFERENCES

FIELD

The invention relates to mass spectrometry and to a method of comparing mass spectra.

INTRODUCTION

Mass spectrometers are often used to analyze test samples that include many different species or compounds of interest. Typically, MS/MS analysis is used to (1) select a precursor or parent ion of interest, (2) fragment that ion, and then (3) conduct further analysis of these fragment ions. For example, an MS/MS system might include a first ion guide, which axially ejects the parent ion of interest into a collision cell. Once in the collision cell, the parent ion is fragmented and the fragments are ejected to a downstream mass spectrometer which can be used to identify the fragment ions of interest. Optionally, these fragment ions could be further fragmented.

SUMMARY

In accordance with an aspect of the present invention there is provided a method of processing mass spectrographic data regarding reaction pairs in an ion sample. The method comprises (a) obtaining a first mass spectrum of the ion sample; (b) obtaining a second mass spectrum of the ion sample; (c) selecting a neutral difference; and, (d) shifting the second mass spectrum by the neutral difference relative to the first mass spectrum of the ion sample to provide a shifted mass spectrum, and then comparing the shifted mass spectrum with the first mass spectrum of the ion sample to determine at least one reaction pair based on the neutral difference.

In accordance with a further embodiment of the present invention there is provided a mass analysis system for obtaining and processing mass spectrographic data regarding reaction pairs in an ion sample. The mass analysis system comprises (a) a mass spectrometer system for obtaining a first mass spectrum and a second mass spectrum of the ion sample; (b) a neutral difference selector for selecting a neutral difference; and, (c) a processor for shifting the second mass spectrum by the neutral difference relative to the first mass spectrum of the ion sample to provide a shifted mass spectrum and then comparing the shifted mass spectrum with the first mass spectrum of the ion sample to determine at least one reaction pair based on the neutral difference.

In accordance with a yet further embodiment of the present invention there is provided a computer program product for processing mass spectrographic data regarding the reaction pairs in an ion sample. The computer program product comprises a recording medium and means recorded on the recorded medium to instruct the computer system to perform the steps of; (a) receiving a first mass spectrum of the ion sample; (b) receiving a second mass spectrum of the ion sample; (c) selecting a neutral difference; and, (d) shifting the second mass spectrum by the neutral difference relative to the first mass spectrum of the ion sample to provide a shifted mass spectrum and then comparing the shifted mass spectrum with the first mass spectrum of the ion sample to determine at least one reaction pair based on the neutral difference.

These and other features of the applicants' teachings are set forth herein.

BRIEF DESCRIPTION OF THE DRAWINGS

The skilled person in the art will understand that the drawings, described below, are for illustration purposes only. The drawings are not intended to limit the scope of the applicant's teachings in anyway.

DETAILED DESCRIPTION OF VARIOUS EMBODIMENTS

Figure 1:
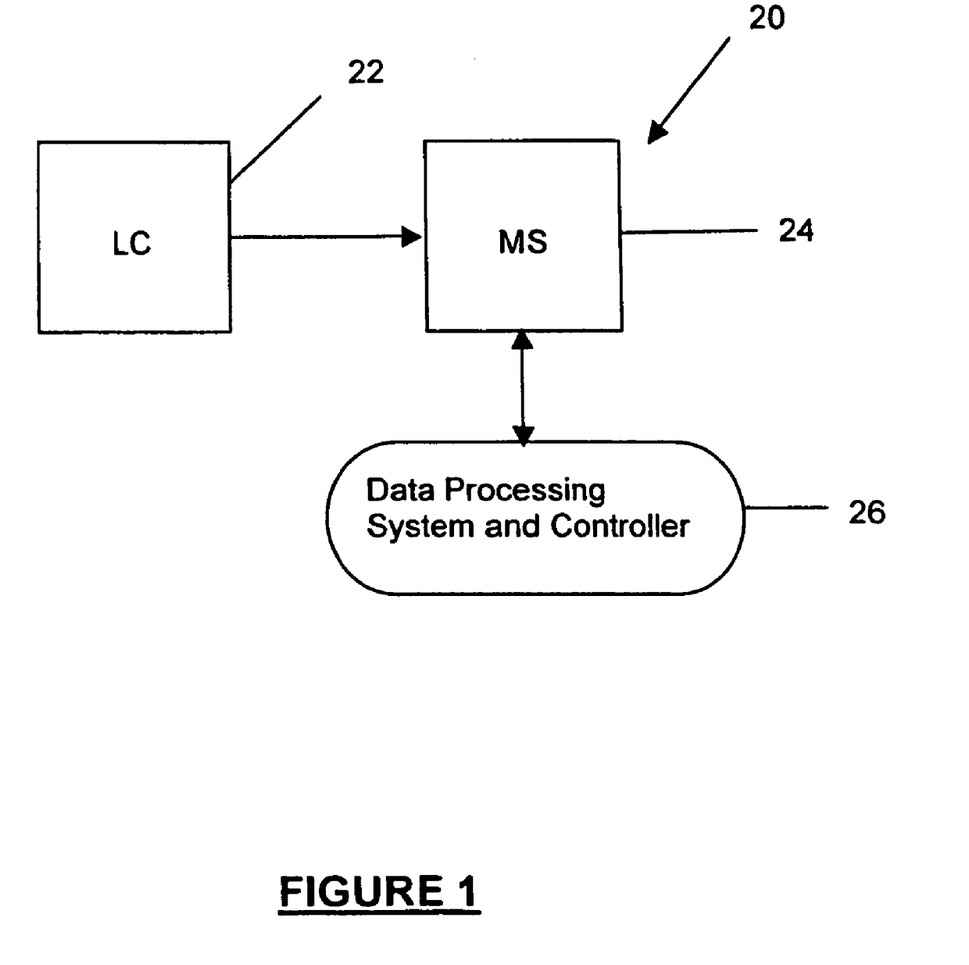
FIG. 1, in a block diagram, illustrates a liquid chromatography, mass spectrometry (LCMS) system in accordance with an aspect with the present invention.

Referring to FIG. 1, there is illustrated in a block diagram a mass analysis system 20 in accordance with an aspect of the present invention. The mass analysis system 20 comprises a chromatography column 22 coupled to a mass spectrometer component 24, which may be either a single mass spectrometer, or a tandem mass spectrometry system capable of conducting multiple stages of mass spectrometry. These two components may be provided, for example, by the API 3000™, the API 4000™, the 3200 QTRAP or the 4000 QTRAP LC/MS/MS system marketed by MDS Sciex although those skilled in the art will appreciate that the invention can be applied to any system that has MS and MS/MS capabilities. A data-processing system and controller 26 controls the operation of the MS component 24 and extracts information from the mass spectra obtained by the MS component 24. The LC portion of the LC/MS/MS system is optional as the ions could also be provided by infusion, or other means, such as, for example an ion source such as Matrix Assisted Laser Desorption/Ionization (MALDI).

Figure 2:
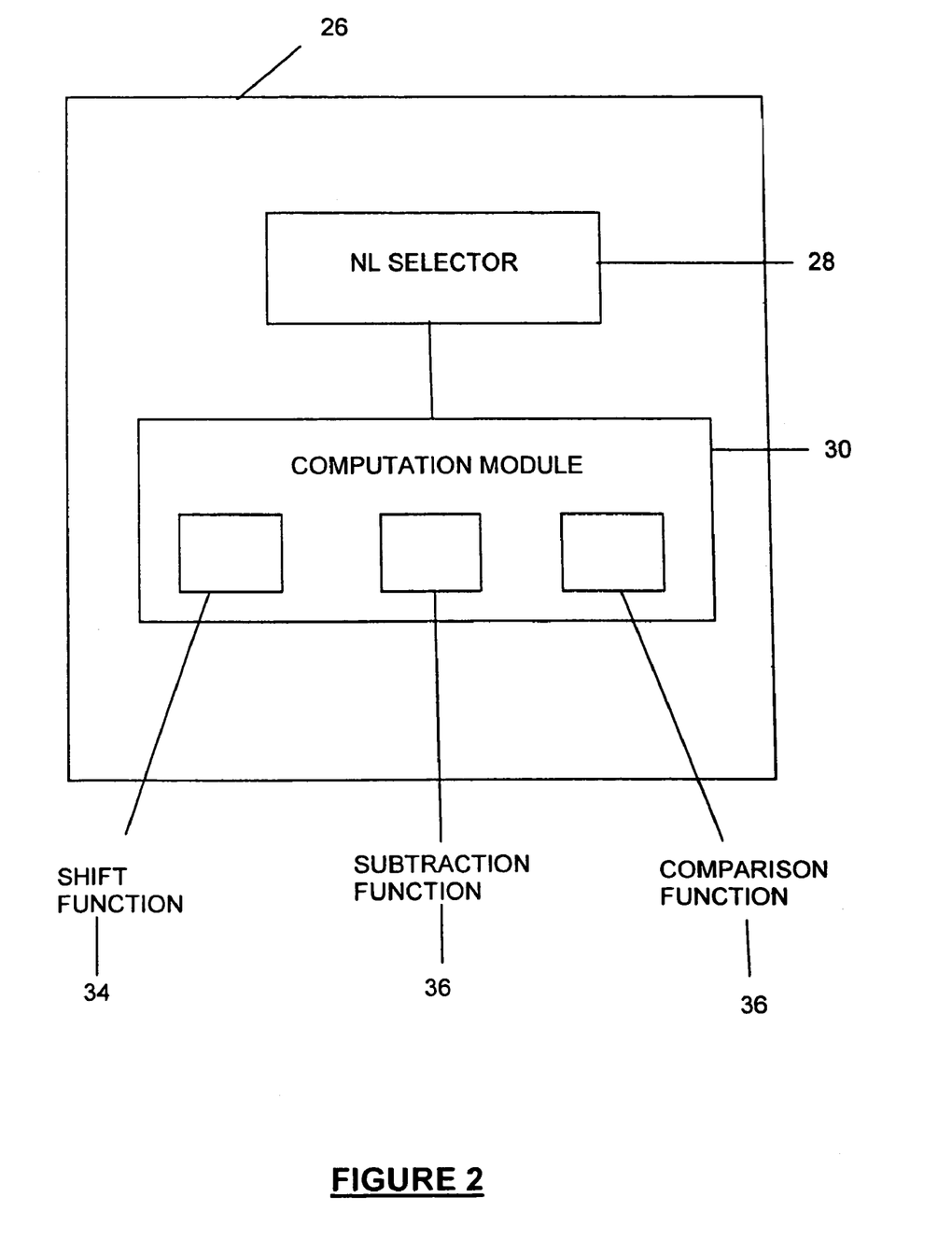
FIG. 2, in a block diagram, illustrates the controller of FIG. 1.

Referring to FIG. 2, the data processing system and controller 26 of FIG. 1 is illustrated in more detail. As shown, the data processing system and controller 26 comprises a neutral loss (NL) selector for selecting a particular neutral loss of interest. As described in greater detail below, the selection of the neutral loss may be automated, or may be by a user via a suitable user input device. The neutral loss selector 28 is linked with a computation module 30 to provide the neutral loss or neutral losses selected to this computation module 30. The computation module 30 in turn comprises a shift function 32, a comparison function 34 and a subtraction function 36.

The data processing system and controller 26 may be provided by a general purpose computing device, such as for example without limitation, a desk top computer, slim line computer, laptop computer, workstation computer or other similar computer device. Such a general computing system may include the following components; a network interface, a display, a memory store, input means, a central processing unit and a bus. The general purpose computing system may communicate with a network, which may also be connected to other similar computing systems.

In cases where the data processing system and controller 26 is provided by a general computing system, the general computing system may be configured to provide the components of the data processing system and controller 26 shown in FIG. 2 by a suitable software product including a recording medium, together with means recorded on the recording medium to configure the memory store and central processing unit of the general unit computing device to provide the neutral loss selector 28, computation module 30, shift function 32, comparison function 34 and subtraction function 36 described above. In other embodiments, the data processing system and controller 26 may be provided by a dedicated computing device with no need for external software to configure it suitably.

Optionally, a data processing system and controller 26 may not be linked to the mass spectrometer component 24, instead being used for post-acquisition processing of the data previously stored from the mass spectrometer system.

In operation, the MS component 24 obtains two mass spectrographic scans for the same sample. One scan is a low orifice (low fragmentation) scan in which large amounts of the parent ion will be present, together with small amounts of fragment ions. The second large orifice (high fragmentation) scan is conducted with the same ion sample. Due to fragmentation, the mass spectrum obtained from the high fragmentation scan will contain less of the parent ion and more of the fragment ions than the mass spectrum obtained from the low fragmentation scan. Alternatively, a collision cell may also be used to acquire mass spectra at different levels of fragmentation. For example, a first mass analyzer operated in RF-only mode may focus ions into a collision cell operated at a minimal collision energy for transmission of low fragmentation ions and at higher collision energy to generate fragmentation ions. Then, from the collision cell, the ions can be provided to a second mass analyzer, or ejected back to the first mass analyzer, for mass analysis of the population of ions sequentially generated in the collision cell (i.e., low fragmentation ions and high fragmentation ions).

Typically, mass spectra are shrunk by subtracting out zero values in the spectra. However, according to aspects of the present invention, these zero values are retained in both the low fragmentation mass spectrum and the high fragmentation mass spectrum for reasons that will be outlined below.

The low fragmentation mass spectrum and the high fragmentation mass spectrum are communicated to the computation module 30 of the data processing system and controller 26. Within the computation module 30, the subtraction function 36 subtracts the low fragmentation mass spectrum from the high fragmentation mass spectrum to obtain a differential mass spectrum. This step removes a lot of the noise that is common to both the low fragmentation mass spectrum and the high fragmentation spectrum, thereby increasing the relative mass signals for the fragment ion of interest in the differential mass spectrum, as the low fragmentation mass spectrum will not have as much of this fragment ion as the high fragmentation mass spectrum. According to some embodiments, this subtraction step can be bypassed. Specifically, where the ion samples received by the MS component 24 are very clean (and the concentration of the analyte is high), it may not be necessary to clean up the ion sample by subtracting the low fragmentation mass spectrum from the high fragmentation mass spectrum. This could be achieved, for example, by extending the LC separation step in the liquid chromatography column 22 upstream from the mass spectrometer component 24.

At some point, a neutral loss of interest is selected by either (1) a user through a user input means, or (2) automatically by the system as it runs through a number of possible neutral losses of interest.

Subsequent to both the selection of the neutral loss by the neutral loss selector 28, and the derivation of the differential mass spectrum by the subtraction function 36, the shift function 34 shifts the mass signals of the differential mass spectrum by the selected neutral loss, such that the mass signals for the fragment ions in the differential mass spectrum now align with the mass signals for the parent ion in the minimal fragmentation mass spectrum. Then, the mass signals of the shifted differential mass spectrum are compared with the aligned or corresponding mass signals of the low fragmentation mass spectrum by the comparison function 36. Preferably, this comparison multiplies the aligned mass signals of the shifted differential mass spectrum and the low fragmentation mass spectrum, such that, for example, the mass signals for fragment ions in the shifted differential mass spectrum are multiplied by the mass signals for the parent ions in the low fragmentation mass spectrum. By this means, noise is further removed as unless two mass signal peaks align, the resulting product would be very close to zero. Thus, the product spectrum obtained by multiplying the shifted differential mass spectrum with the minimal fragmentation mass spectrum will typically contain fewer peaks, making it easier to select the ion of interest for further processing.

Figure 3:
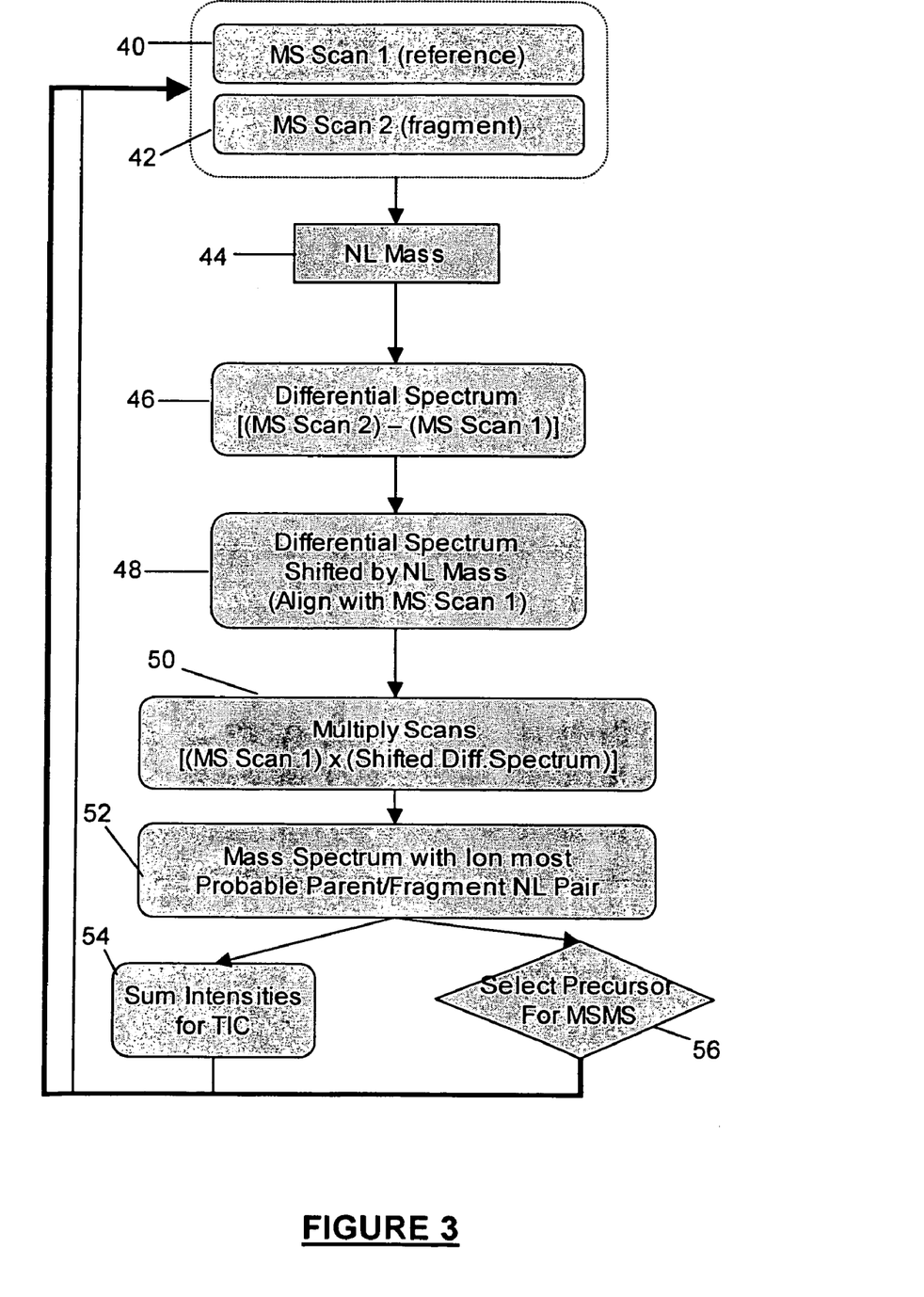
FIG. 3, in a process flow diagram, illustrates a method of processing mass spectrographic data regarding parent/fragment pairs in an ion sample in accordance with a further aspect of the invention.

Referring to FIG. 3, there is illustrated in a process flow diagram a method of processing mass spectrographic data regarding parent/fragment pairs in an ion sample in accordance with a preferred aspect of the invention. In step 40, a reference spectrum is obtained from a first MS scan of an ion sample. In step 42, a high fragmentation mass spectrum from a second MS scan is obtained for the ion sample. Typically, fragmentation will be induced for the second MS scan either at source or in a collision cell, such that the mass spectrum of the second MS scan will be fragmented to a much greater extent than the reference spectrum obtained from the first MS scan.

Figure 4A:
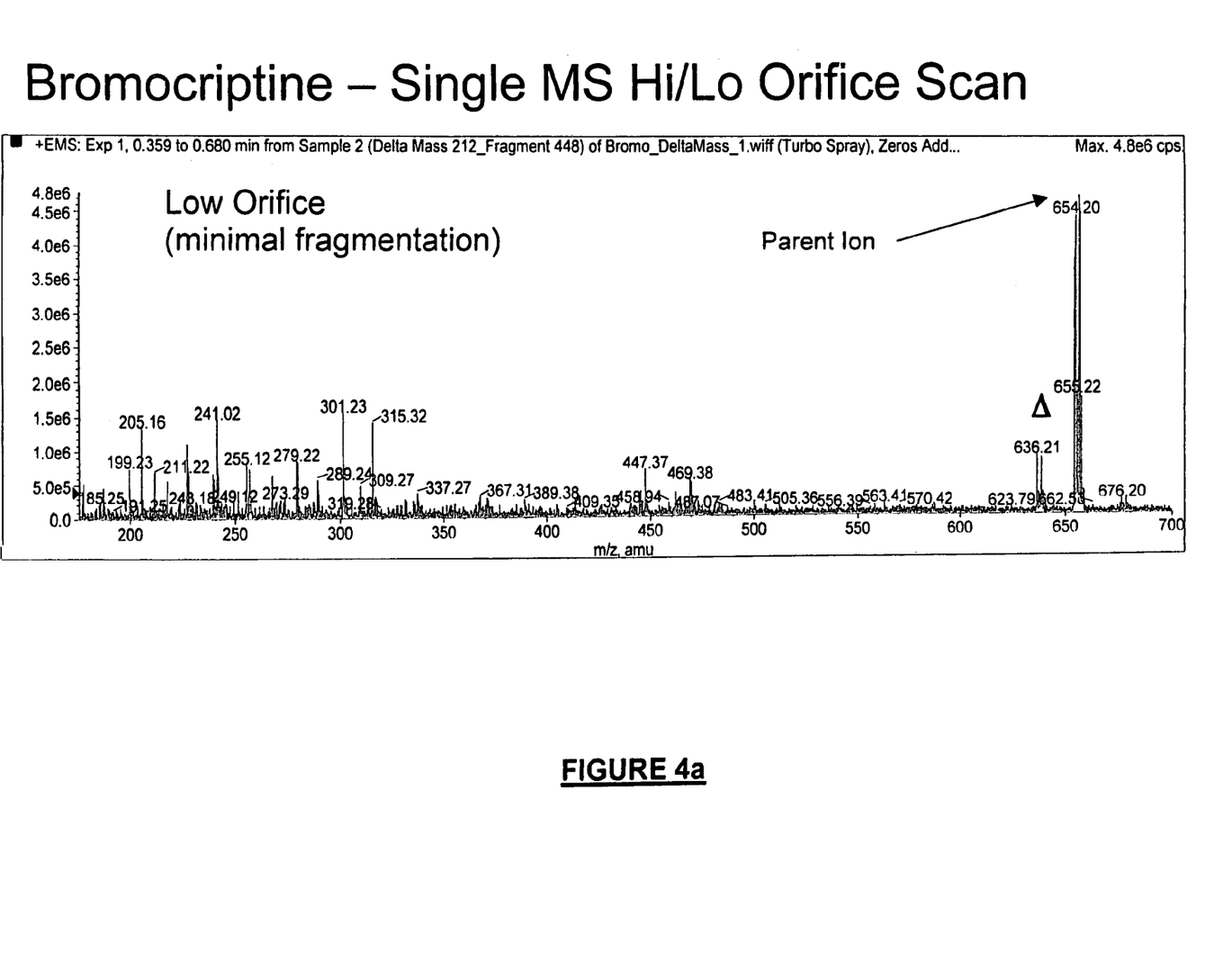
FIGS. 4a and 4b, illustrate scans of a Bromocriptine-containing ion sample at different levels of fragmentation obtained in accordance with an implementation of the method of FIG. 3.
Figure 4B:
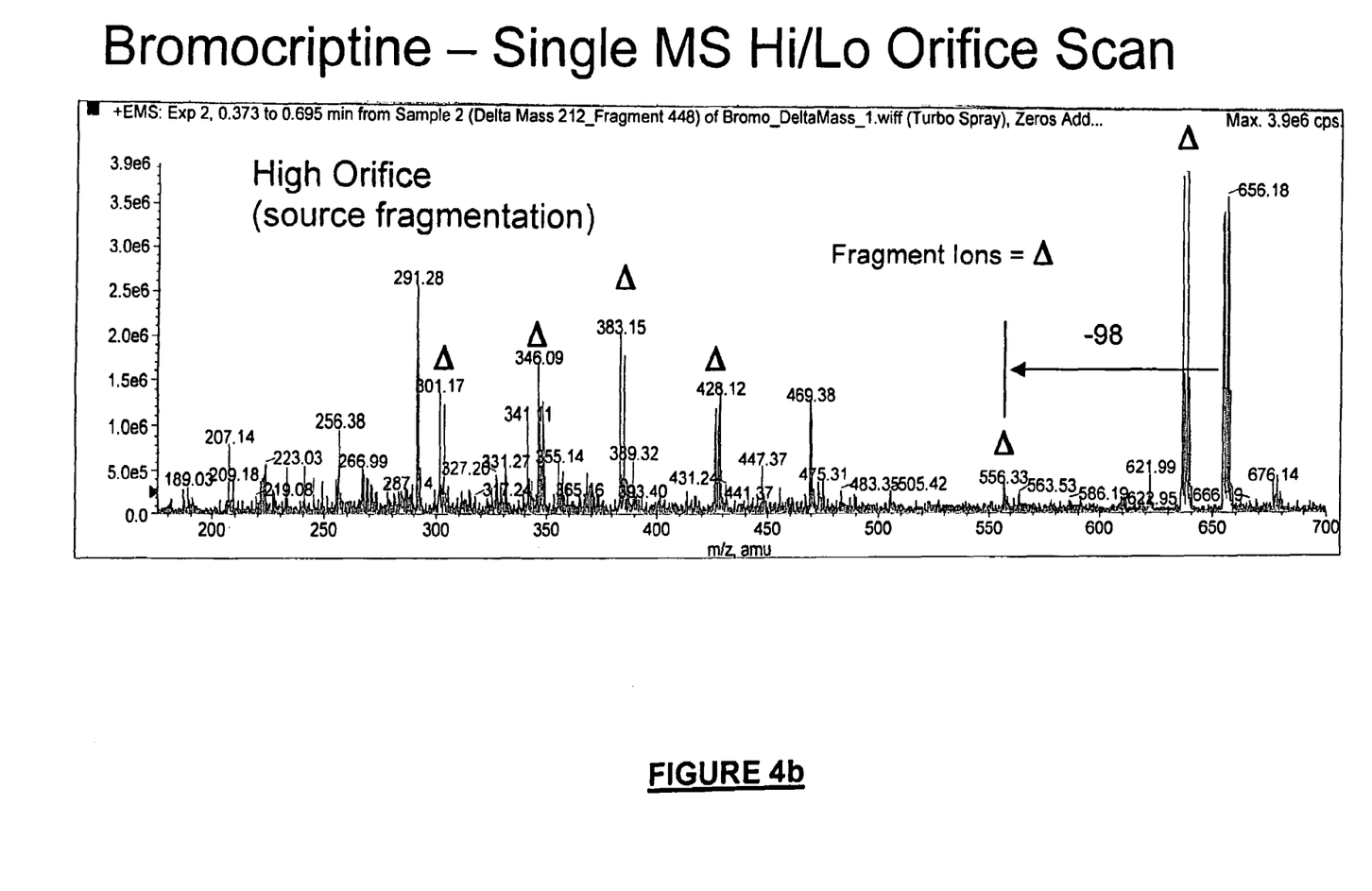

Referring to FIGS. 4a and 4b, mass spectra obtained from a low orifice scan of an ion sample containing Bromocriptine are illustrated. Specifically, FIG. 4a illustrates the reference spectrum (the low orifice or low fragmentation spectrum) while FIG. 4b illustrates the high fragmentation mass spectrum (from a high orifice scan). Both of these mass spectra are obtained from the same ion sample. In step 44, a neutral loss mass is selected. Optionally, several neutral losses may be selected by a user, or the selection of these neutral losses may be automated. In step 46 a differential spectrum is obtained by subtracting the reference spectrum obtained in step 40 from the high fragmentation spectrum obtained in step 42. In doing so, it is important to retain the "zeros" in both initial spectra in order to provide proper alignment of mass signals.

Figure 5A:
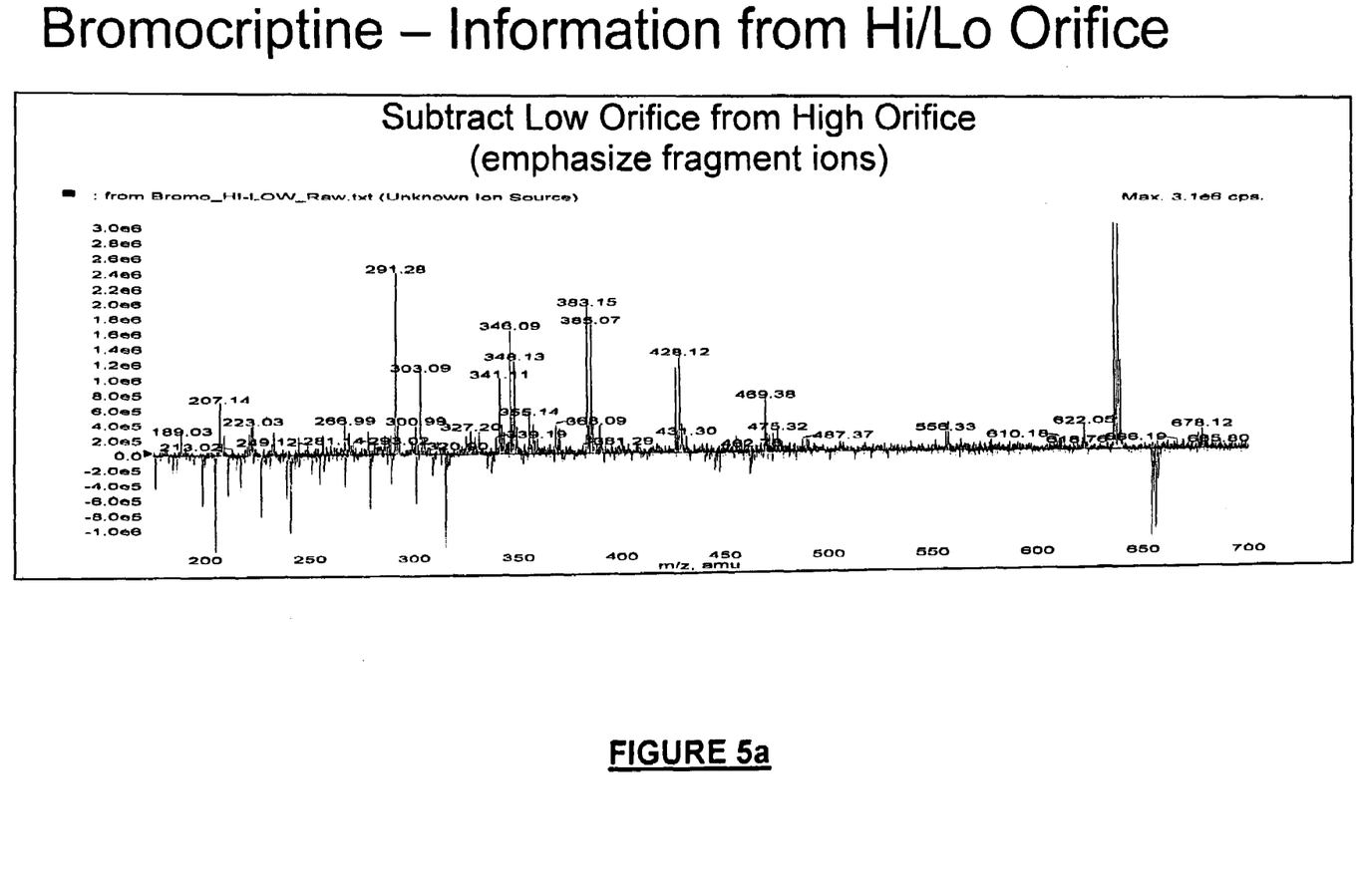
FIGS. 5a and 5b, illustrate mass spectra derived from the mass spectra of FIGS. 4a and 4b in accordance with a particular implementation of the method of FIG. 3 using a neutral loss of 98.

Referring to FIG. 5a, a differential mass spectrum obtained by subtracting the mass spectrum of FIG. 4a from the mass spectrum of FIG. 4b is illustrated. As shown, subtracting the reference spectrum, which contains comparatively more of the parent and comparatively less of the fragment ions, will emphasize mass signal peaks for the fragment ions.

Figure 5B:
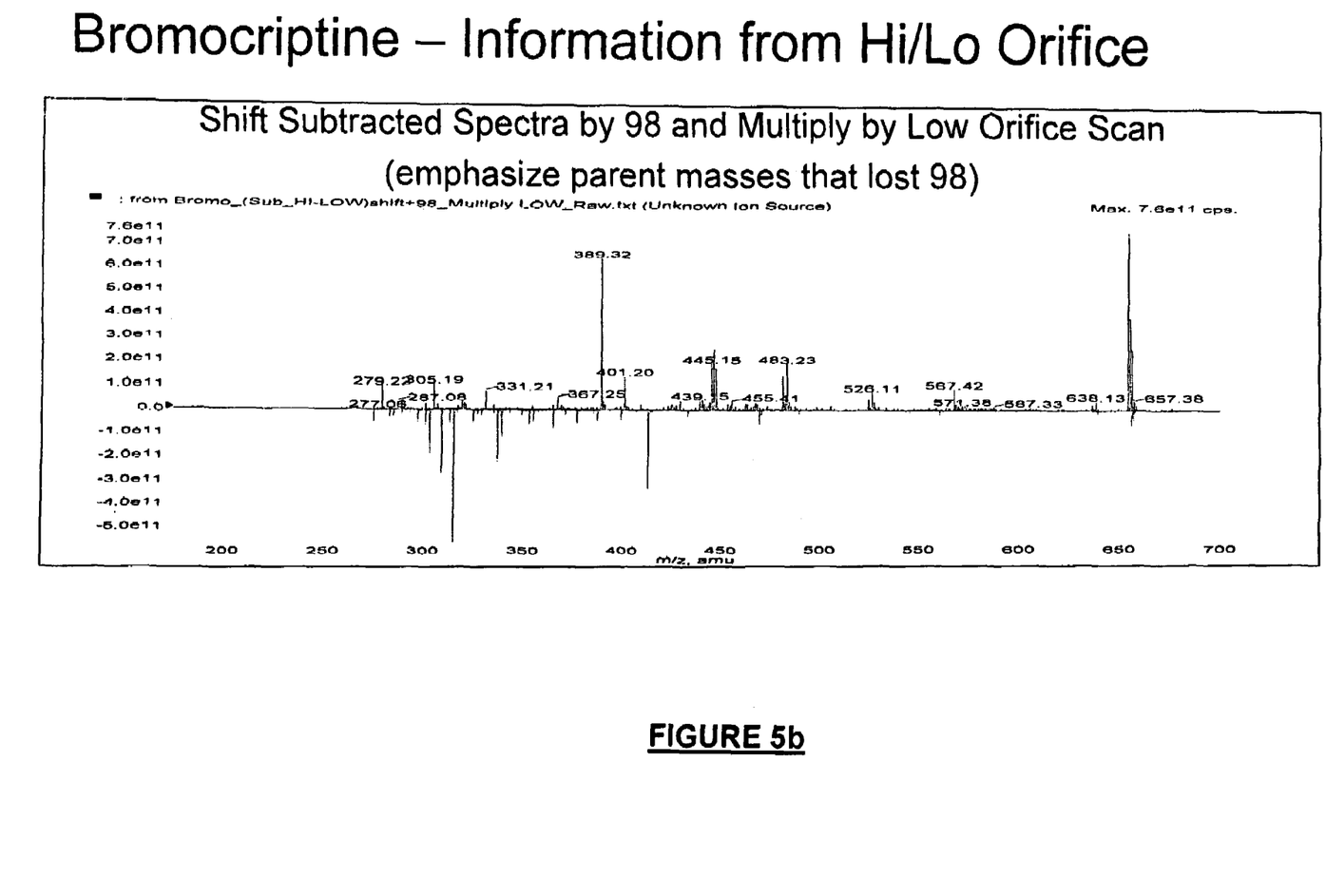

In step 48 of the method of FIG. 3, the differential spectrum determined in step 46 is shifted by the neutral loss selected in step 44 such that the mass signals for fragments indicated by the neutral loss selected are aligned with the mass signals for the parent ions in the reference spectrum. Then, this shifted differential spectrum obtained in step 48 is, in step 50, multiplied with the reference spectrum. This step of multiplying the two mass spectra involves multiplying each mass signal in one spectrum with the corresponding aligned mass signal in the other spectrum to obtain a probability mass spectrum. Such a probability mass spectrum is illustrated in FIG. 5b. From FIG. 5b, it is apparent that this probability mass spectrum indicates the most probable associated parent/fragment pairs for the neutral loss selected in step 44. That is, the peak intensity in the probability mass spectrum shown in FIG. 5b is proportional to the probability of the ions in the initial spectra representing parents and fragments for that neutral loss mass. The selection of the neutral loss mass parent/fragment pairs occurs in step 52. This step may be performed manually, by selecting the mass signal peaks in the probability mass spectrum. Alternatively, this step may be automated by selecting all mass signal peaks in the probability mass spectrum that are over a selected threshold in height. In either case, the parent/fragment pairs can then be determined. Typically, these parent/fragment pairs will reflect, at least in the case of biological samples, the presence of related classes of compounds (e.g. metabolites or post-translational modification). In step 54, the intensities of all of the parent/fragment pairs can be summed to determine a total ion current plot (TIC). Concurrently, in step 56, the precursor corresponding to the parent/fragment pair can be selected as the ion for subsequent downstream MS/MS analysis. Then, optionally the method can return to steps 40 and 42 for a new ion sample.

Figure 6A:
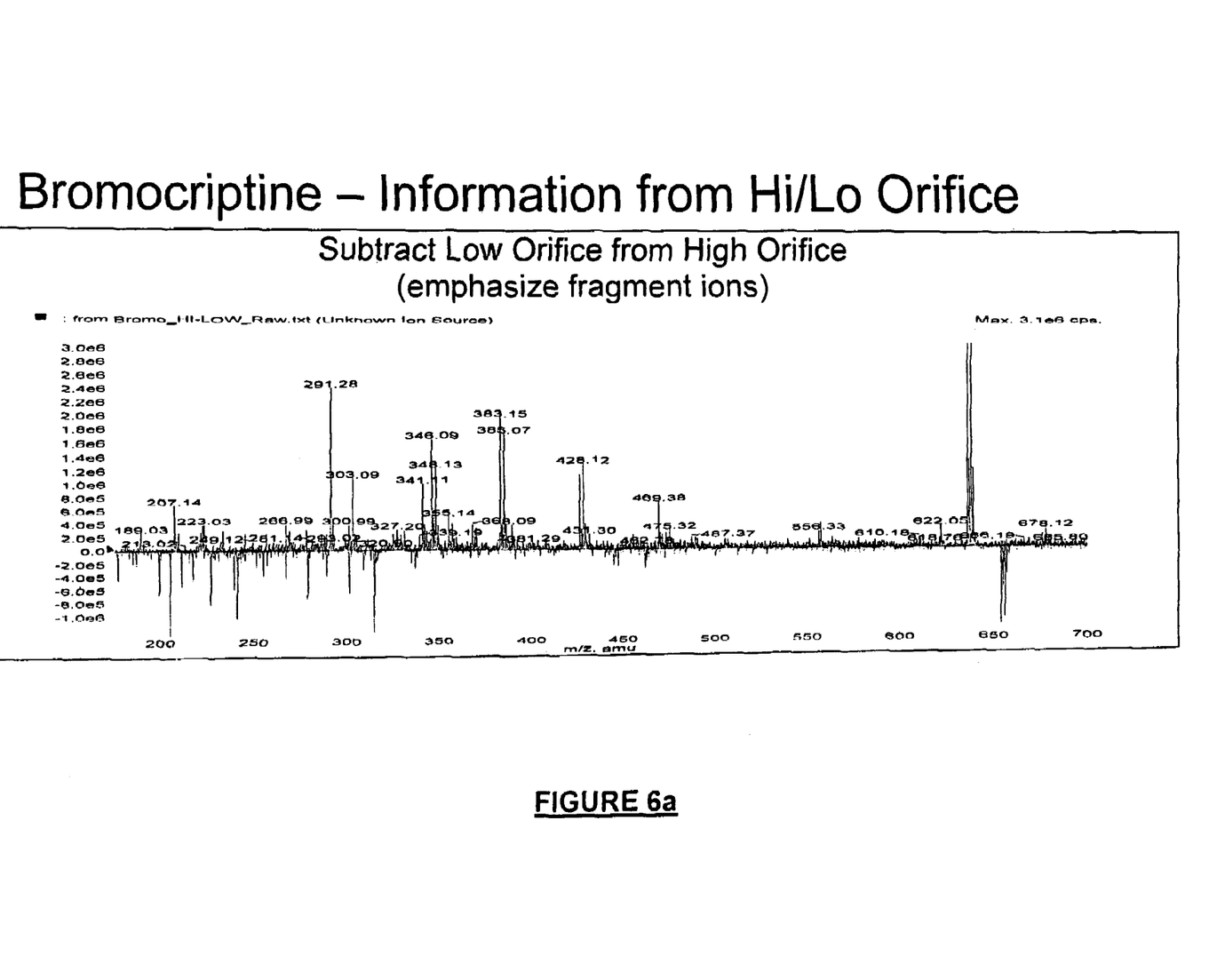
FIGS. 6a and 6b, illustrate mass spectra derived from the mass spectra of FIGS. 4a and 4b in accordance with a further particular implementation of the method of FIG. 3 using a neutral loss of 24; and, FIG. 7, in a process flow diagram, illustrates a method of processing mass spectrographic data regarding parent/fragment pairs in an ion sample in accordance with a further aspect of the present invention.
Figure 6B:
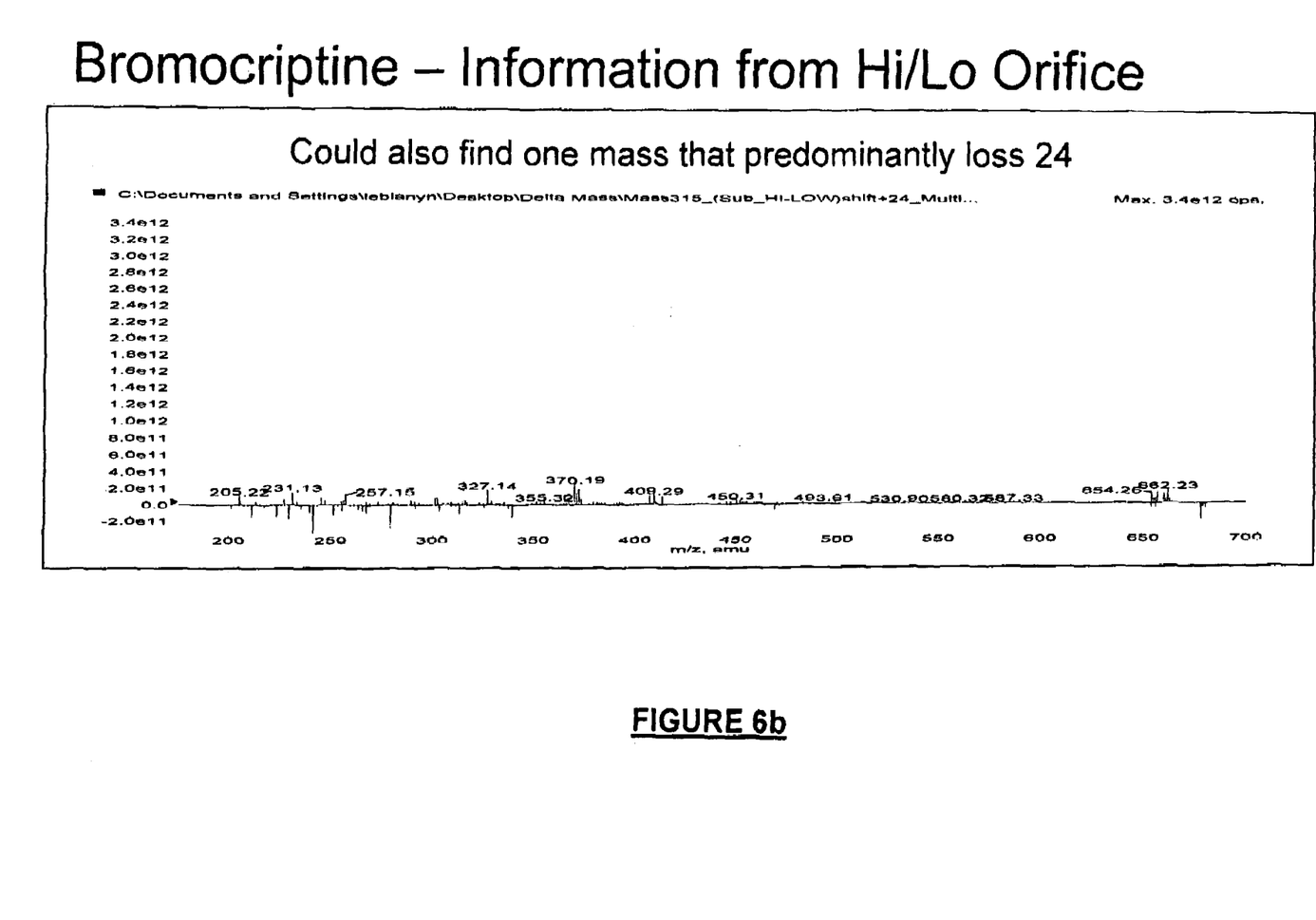

Alternatively, after steps 54 and 56, a new neutral loss may be selected and steps 48 to 56 repeated for the same ion sample for this new neutral loss. For example, as illustrated in FIGS. 6a and 6b, the mass spectra of FIGS. 4a and 4b may be analyzed using a different selected neutral loss of 24. The differential mass spectrum shown in FIG. 6a, will, of course, be the same as the differential mass spectrum previously determined with a selected neutral loss of 98. However, when this differential mass spectrum is shifted by the neutral loss and then multiplied by the mass spectrum of FIG. 4a, then a new probability mass spectrum, shown in FIG. 6b, will be obtained. This probability mass spectrum enables different parent/fragment pairs—identified by the neutral loss of 24—to be identified. That is, the ion signal density in the probability mass spectrum shown in FIG. 6b is proportional to the probability of the ions in the initial spectra representing parents and fragments for a neutral loss of 24. As described above, in step 54, the intensities of all of the parent/fragment pairs can then be summed to determine the TIC. Concurrently, in step 56, the precursor corresponding to the parent/fragment pair of a given neutral loss can be selected as the ion for subsequent downstream MS/MS analysis.

The first mass spectrum shown in FIG. 4a comprises a sequence of first mass signals defined over a mass axis (the X axis in FIG. 4a) such that each mass signal in FIG. 4a represents an associated signal magnitude for an associated mass on the mass axis. Similarly, the mass spectrum of FIG. 4b comprises a sequence of mass signals defined over the mass axis (again the X axis) such that each mass signal represents an associated signal magnitude for an associated mass on the mass axis.

As described above, the mass spectrum of FIG. 4a is subtracted from the mass spectrum of FIG. 4b. This involves subtracting each individual mass signal in the sequence of mass signals of FIG. 4a from a corresponding aligned (at the same point along the X axis) mass signal in the sequence of mass signals of the mass spectrum of FIG. 4b.

As described above in step 48 in the method of FIG. 3, the differential spectrum obtained by subtracting the mass spectrum of FIG. 4a from the mass spectrum of FIG. 4b is shifted by the neutral loss selected in step 44. This entails displacing a sequence of mass signals of the differential mass spectrum along the mass axis by the neutral loss relative to the sequence of mass signals of the mass spectra of either FIG. 4a or FIG. 4b. In other words, it may optionally be the mass spectra of FIG. 4a or FIG. 4b that is shifted and not the mass signals of the differential mass spectrum provided these mass signals are shifted by the neutral loss relative to each other. Then, the sequence of mass signals of the shifted differential mass spectrum is compared with a sequence of mass signals of one of the mass spectra of FIGS. 4a and 4b to determine at least one parent/fragment pair associated with neutral loss of interest. To compare the sequence of mass signals of the shifted differential mass spectrum with the sequence of mass signals of either FIG. 4a or FIG. 4b, an individual shifted differential mass signal in the sequence of shifted differential mass signals of the shifted differential mass spectrum is compared with the individual mass signal in the sequence of mass signals of the first mass spectrum that is aligned with the individual shifted differential mass signal along the mass axis of the two mass spectra. In some embodiments, as described above, this involves multiplying the individual shifted differential mass signal with the corresponding aligned individual mass signal of FIG. 4a or 4b. Preferably, this is done for all of the aligned mass signals for these two mass spectra.

Figure 7:
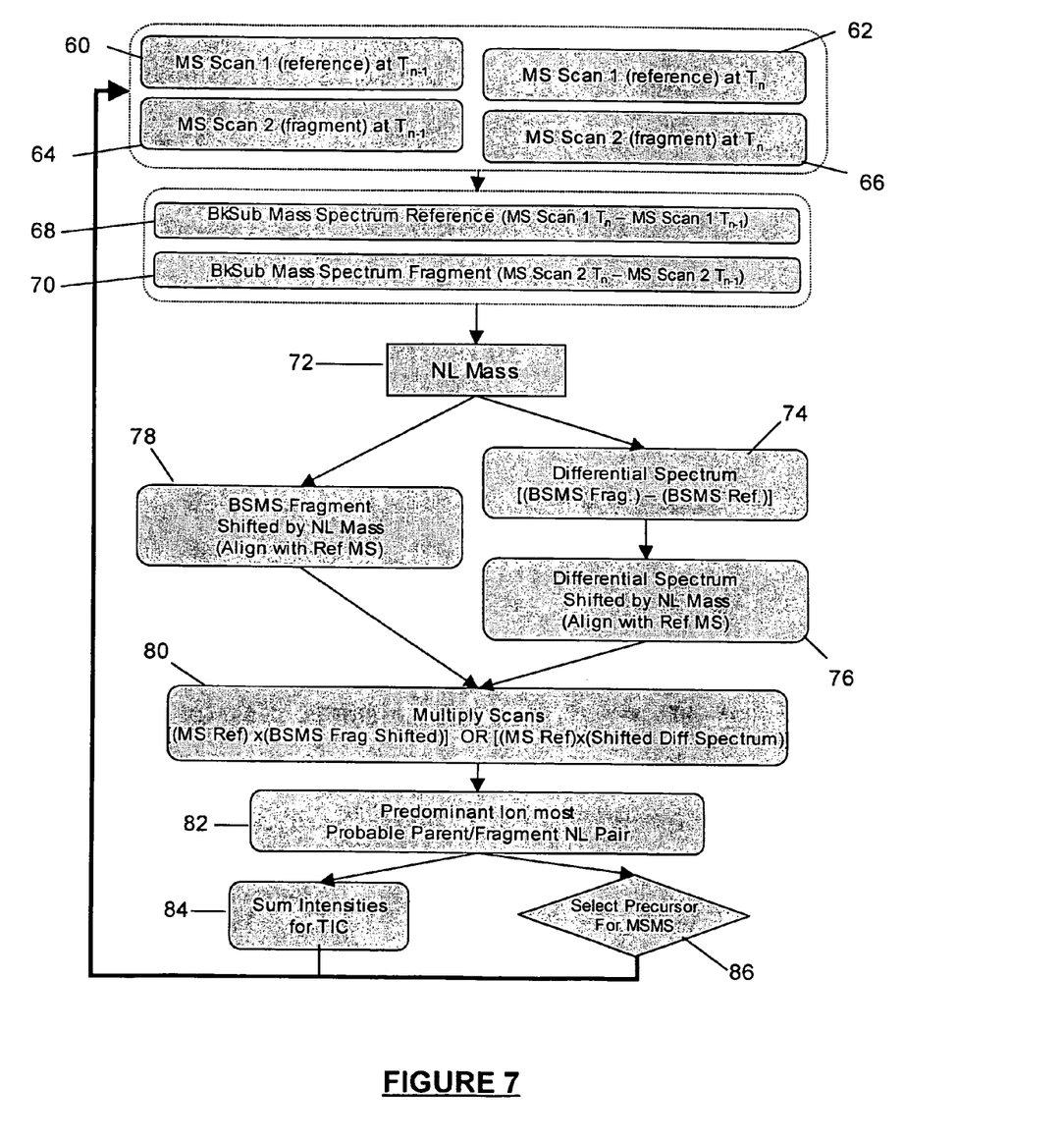

Referring to FIG. 7, there is illustrated in a process flow diagram a method of processing mass spectrographic data regarding parent/fragment pairs in an ion sample in accordance with a further aspect of the invention. This further aspect of the invention involves multiple processing cycles for both the low fragmentation or reference spectrum and the high fragmentation spectrum. That is, in the aspect of the invention illustrated in FIG. 7, the ion sample for both the low fragmentation and high fragmentation mass spectra is processed or cycled several times. In this aspect of the invention, a $T_{n-1}$ reference mass spectrum is obtained from a mass spectrum scan of the ion sample in step 60, and the $T_n$ reference spectrum is obtained from the mass spectrum scan of the ion sample in the next cycle in step 62. Similarly, a $T_{n-1}$ high fragmentation mass spectrum is obtained from a high fragmentation mass spectrum scan for the ion sample in step 64, and, subsequently, a $T_n$ high fragmentation mass spectrum is obtained from the high fragmentation mass spectrum scan of the ion sample in the next cycle in step 66. As described above, fragmentation will typically be induced for the high fragmentation mass spectrum scans either at source or in a collision cell, such that the high fragmentation mass spectrums obtained in steps 64 and 66 will be a result of ions being fragmented to a much greater extent than the reference spectrums obtained from the first mass spectrum scans in steps 60 and 62.

In step 68 a filtered reference mass spectrum is obtained by subtracting the $T_{n-1}$ mass spectrum obtained in step 60 from the $T_n$ mass spectrum obtained in step 62. Similarly, a filtered high fragmentation mass spectrum is obtained in step 70 by subtracting the $T_{n-1}$ high fragmentation mass spectrum obtained in a step 64 from the $T_n$ high fragmentation mass spectrum obtained in step 66. Steps 68 and 70 help to clean up the reference and high fragmentation mass spectra by filtering out some of the noise that is common to both the $T_{n-1}$ and $T_n$ mass spectrum scans.

In step 72, a neutral loss mass is selected. Optionally, as described above in connection with FIG. 3, several neutral losses may be selected by a user, or the selection of these neutral losses may be automated. In step 74, a differential spectrum is obtained by subtracting the filtered or background subtracted mass spectrum (BSMS) reference spectrum obtained in step 68 from the filtered or BSMS high fragmentation mass spectrum obtained in step 70. As discussed above, in performing the subtraction of step 74 it is important to retain the "zeros" in both BSMS spectra in order to provide proper alignment of mass signals. In step 76, the differential spectrum obtained in step 74 is shifted by the neutral loss selected in step 72 such that the mass signals for fragments indicated by the neutral loss selected are aligned with the mass signals for the parent ions in the BSMS reference spectrum.

Due to the fact that the reference and high fragmentation mass spectra have been cleaned up in steps 68 and 70, step 78 can be implemented on its own or one can further clean the spectra by implementing steps 74 and 76. In step 78, the BSMS fragment spectrum obtained in step 70 is shifted by the neutral loss mass relative to the reference mass spectrum. Whichever path taken from step 72, whether through step 78 on the one hand, or steps 74 and 76 on the other, the method of FIG. 7 then proceeds to step 80.

In step 80, either the shifted BSMS high fragmentation mass spectrum obtained in step 78, or the shifted differential mass spectrum obtained in step 76 is multiplied by the reference mass spectrum generated in either step 62 or step 68. As described above, this step of multiplying the two mass spectra involves multiplying each mass signal in one mass spectrum with the corresponding aligned mass signal in the other mass spectrum to obtain a probability mass spectrum. In this probability mass spectrum, the mass signal peak intensity is proportional to the probability of the ions in the initial mass spectra input in step 80 representing precursor ions associated with a parent/fragment pair for that neutral loss mass. In step 82, the most probable parent/fragment pairs for the selected neutral loss are themselves selected. Then, in step 84, the intensities of all of the parent/fragment pairs can be summed to determine a TIC. Concurrently, in step 86, parent/fragment pairs can be selected as the precursors for subsequent downstream MS/MS analysis. Then, optionally, the method can return to steps 60, 62, 64, 66 for a new ion sample. Alternatively, after steps 84 and 86 a new neutral loss may be selected and steps 74 to 86 repeated for this new neutral loss.

Other variations and modifications of the invention are possible. For example, as described above, in some embodiments it will not be necessary to clean up the either the low fragmentation or reference mass spectrum or the high fragmentation mass spectrum. Specifically, where the ion sample is very clean, or the concentration of the analyte is high, it may be unnecessary to clean up the ion sample by subtracting the background mass spectrum. Further, while the above-described aspects of the invention have been described in connection with neutral loss, other aspects of the invention may also be applied to neutral gain. In such embodiments, the precursor ions would be subjected to ion reactions, instead of being fragmented, which may generate adducts. More generally, different aspects of the invention relate to neutral differences, whether positive or negative, and either parent/fragment pairs, or parent/adduct pairs, referred to generally as reaction pairs may be generated. The parent/fragment pairs may be generated, for example, by fragmentation via collision, while the adduct pairs can be formed via reaction in gas phase. In addition, in connection with aspects of the invention described above relating to neutral loss, the description has for the most part focused on instances in which the minimal fragmentation scan is acquired first, and the higher fragmentation scan subsequently acquired. This can clearly be advantageous in some situations as the same ions can be scanned both before and after fragmentation. However, in other aspects of the invention, the high fragmentation scan may be obtained before, or at the same time as, the low fragmentation scan. All such modifications or variations are believed to be within the sphere and scope of the invention as defined by the claims appended hereto.

The invention claimed is:

1. A method of processing mass spectrographic data regarding reaction pairs in an ion sample, the method comprising:
   a) obtaining a first mass spectrum of the ion sample;
   b) obtaining a second mass spectrum of the ion sample wherein one of a) and b) comprises subjecting the ion sample to at least one of fragmentation and reaction such that the first mass spectrum differs from the second mass spectrum;
   c) selecting a neutral difference; and,
   d) shifting the second mass spectrum by the neutral difference relative to the first mass spectrum of the ion sample to provide a shifted mass spectrum and then comparing the shifted mass spectrum with the first mass spectrum of the ion sample and determining at least one reaction pair based on the neutral difference, wherein the first mass spectrum comprises a sequence of first mass signals defined over a mass axis such that each first mass signal represents an associated first signal magnitude for an associated mass on the mass axis;
   the second mass spectrum comprises a sequence of second mass signals defined over the mass axis such that each second mass signal represents an associated second signal magnitude for an associated mass on the mass axis; and,
   step (d) comprises displacing a sequence of mass signals of the second mass spectrum along the mass axis by the neutral difference relative to the sequence of first mass signals of the first mass spectrum and then comparing a sequence of mass signals of the shifted mass spectrum with the sequence of first mass signals of the first mass spectrum and determining the at least one reaction pair.

2. The method as defined in claim 1 wherein the neutral difference selected in step (c) is a neutral gain.

3. The method as defined in claim 1 wherein the neutral difference selected in step (c) is a neutral loss.

4. The method as defined in claim 3 wherein step (c) comprises selecting a plurality of neutral losses; and
   step (d) comprises, for each neutral loss in the plurality of neutral losses, displacing the sequence of mass signals of the second mass spectrum by the neutral loss along the mass axis relative to the first sequence of mass signals to obtain an associated shifted spectrum and then comparing the sequence of mass signals of the associated shifted spectrum with the first mass spectrum of the ion sample and determining the at least one reaction pair for the neutral loss.

5. The method as defined in claim 3 wherein, in step (d), comparing the sequence of mass signals of the shifted mass spectrum with the sequence of first mass signals of the first mass spectrum and determining the at least one reaction pair for the neutral loss comprises comparing an individual shifted mass signal in the sequence of shifted mass signals of the first mass spectrum, and an individual first mass signal in the sequence of first mass signals of the first mass spectrum, the individual shifted mass signal and the individual first mass signal being aligned along the same mass axis and being a reaction pair of the at least one reaction pair.

6. The method as defined in claim 5 wherein, in step (d), the step of comparing the shifted spectrum with the first mass spectrum and determining the at least one reaction pair based on the neutral loss comprises multiplying the individual shifted mass signal by the individual first mass signal, the individual shifted mass signal and the individual first mass signal being aligned along the same mass axis, to obtain a probability mass spectrum.

7. The method as defined in claim 6 wherein the ion sample is fragmented by a low fragmentation scan in the first mass spectrum and by a high fragmentation scan in the second mass spectrum.

8. The method as defined in claim 3 wherein step (d) further comprises subtracting a reference mass spectrum of the ion sample from the second mass spectrum before shifting the second mass spectrum to obtain the shifted mass spectrum.

9. The method as defined in claim 8 wherein, in step (d), subtracting the reference mass spectrum of the ion sample from the second mass spectrum comprises subtracting an individual reference mass signal in a sequence of reference mass signals of the reference mass spectrum from an individual mass signal in the sequence of second mass signals of the second mass spectrum, the individual shifted mass signal and the individual reference mass signal being aligned along the same mass axis.

10. The method as defined in claim 9 wherein
the ion sample is fragmented by a low fragmentation scan in the first mass spectrum and by a high fragmentation scan in the second mass spectrum; and
the reference mass spectrum is the first mass spectrum.

11. The method as defined in claim 3 wherein
a background mass spectrographic scan is conducted to obtain a background mass spectrum of the ion sample; and,
the background mass spectrum is subtracted from both the first mass spectrum and the second mass spectrum before step (d).

12. A method as defined in claim 1 wherein step (a) and step (b) are not contemporaneous.

13. The method as defined in claim 12 wherein step (a) precedes step (b).

14. A mass analysis system for obtaining and processing mass spectrographic data regarding reaction pairs in an ion sample, the mass analysis system comprising:
a) a mass spectrometer system for obtaining a first mass spectrum and a second mass spectrum of the ion sample by subjecting the ion sample to at least one of fragmentation and reaction such that the first mass spectrum differs from the second mass spectrum;
b) a neutral difference selector for selecting a neutral difference; and,
c) a processor for shifting the second mass spectrum by the neutral difference relative to the first mass spectrum of the ion sample to provide a shifted mass spectrum and then comparing the shifted mass spectrum with the first mass spectrum of the ion sample to determine at least one reaction pair based on the neutral difference, wherein the first mass spectrum comprises a sequence of first mass signals defined over a mass axis such that each first mass signal represents an associated first signal magnitude for an associated mass on the mass axis;
the second mass spectrum comprises a sequence of second mass signals defined over the mass axis such that each second mass signal represents an associated second signal magnitude for an associated mass on the mass axis; and,
the processor is operable to displace a sequence of mass signals of the second mass spectrum along the mass axis by the neutral difference relative to the sequence of first mass signals of the first mass spectrum and then compare a sequence of mass signals of the shifted mass spectrum with the sequence of first mass signals of the first mass spectrum to determine the at least one reaction pair.

15. The mass analysis system as defined in claim 14 wherein
the neutral difference selector is a neutral gain selector, and the neutral difference selected is a neutral gain.

16. The mass analysis system as defined in claim 14 wherein
the neutral difference selector is a neutral loss selector, and the neutral difference selected is a neutral loss.

17. The mass analysis system as defined in claim 16 wherein
the neutral loss selector is operable to select a plurality of neutral losses; and
the processor is operable to, for each neutral loss in the plurality of neutral losses, displace the sequence of mass signals of the second mass spectrum by the neutral loss along the mass axis relative to the first sequence of mass signals to obtain an associated shifted spectrum and then compare the sequence of mass signals of the associated shifted spectrum with the first mass spectrum of the ion sample to determine the at least one reaction pair for the neutral loss.

18. The mass analysis system as defined in claim 16 wherein the processor is operable to compare the sequence of mass signals of the shifted mass spectrum with the sequence of first mass signals of the first mass spectrum by comparing an individual shifted mass signal in the sequence of shifted mass signals of the shifted mass spectrum, and an individual first mass signal in the sequence of first mass signals of the first mass spectrum, the individual shifted mass signal and the individual first mass signal being aligned along the same mass axis.

19. The mass analysis system as defined in claim 18 wherein the processor is operable to compare the shifted spectrum with the first mass spectrum to determine the at least one reaction pair based on the neutral loss by multiplying the individual shifted mass signal by the individual first mass signal, the individual shifted mass signal and the individual first mass signal being aligned along the same mass axis, to obtain a probability mass spectrum.

20. The mass analysis system as defined in claim 15 wherein the ion sample is fragmented by a low fragmentation scan in the first mass spectrum and by a high fragmentation scan in the second mass spectrum.

21. The mass analysis system as defined in claim 16 wherein the processor is operable to subtract a reference mass spectrum of the ion sample from the second mass spectrum before shifting the second mass spectrum to obtain the shifted mass spectrum.

22. The mass analysis system as defined in claim 21 wherein the processor is operable to subtract the reference mass spectrum of the ion sample from the second mass spectrum by subtracting an individual reference mass signal in a sequence of reference mass signals of the reference mass spectrum from an individual mass signal in the sequence of second mass signals of the second mass spectrum, the individual shifted mass signal and the individual reference mass signal being aligned along the same mass axis.

23. The mass analysis system as defined in claim 22 wherein the ion sample is fragmented by a low fragmentation scan in the first mass spectrum and by a high fragmentation scan in the second mass spectrum; and the reference mass spectrum is the first mass spectrum.

24. The mass analysis system as defined in claim 16 wherein the mass spectrometer system is operable to conduct a background mass spectrographic scan to obtain a background mass spectrum of the ion sample; and, the processor is operable to subtract the background mass spectrum from both the first mass spectrum and the second mass spectrum before shifting the second mass spectrum by the neutral loss relative to the first mass spectrum of the ion sample.

25. A computer program product for processing mass spectrographic data regarding reaction pairs in an ion sample, the computer program product comprising a recording medium and means recorded on the recording medium to instruct the computer system to perform the steps of:

a) receiving a first mass spectrum of the ion sample;

b) receiving a second mass spectrum of the ion sample wherein the first mass spectrum is different from the second mass spectrum;

c) selecting a neutral difference; and d) shifting the second mass spectrum by the neutral difference relative to the first mass spectrum of the ion sample to provide a shifted mass spectrum and then comparing the shifted mass spectrum with the first mass spectrum of the ion sample to determine at least one reaction pair based on the neutral difference wherein the first mass spectrum comprises a sequence of first mass signals defined over a mass axis such that each first mass signal represents an associated first signal magnitude for an associated mass on the mass axis;

the second mass spectrum comprises a sequence of second mass signals defined over the mass axis such that each second mass signal represents an associated second signal magnitude for an associated mass on the mass axis; and, step (d) comprises displacing a sequence of mass signals of the second mass spectrum along the mass axis by the neutral difference relative to the sequence of first mass signals of the first mass spectrum and then comparing a sequence of mass signals of the shifted mass spectrum with the sequence of first mass signals of the first mass spectrum and determining the at least one reaction pair.

* * * * *